United States Patent

Kondrat

Patent Number: 6,105,269
Date of Patent: Aug. 22, 2000

[54] OSTEOLOGIC MEASURING DEVICE

[76] Inventor: James W. Kondrat, 311 N. 11th, Wheeling, Ill. 60090

[21] Appl. No.: 08/934,625

[22] Filed: Sep. 19, 1997

[51] Int. Cl.[7] .............................. G01B 5/02; A61B 5/107
[52] U.S. Cl. ............................ 33/512; 033/784; 033/812
[58] Field of Search .............................. 33/452, 464, 512, 33/513, 515, 706, 783, 784, 810, 811, 812

[56] References Cited

U.S. PATENT DOCUMENTS

| | | | |
|---|---|---|---|
| 1,321,567 | 11/1919 | Spindler | 33/812 |
| 1,944,601 | 1/1934 | Gulick | 33/513 |
| 1,976,045 | 10/1934 | Sorenson | 33/513 |
| 3,145,475 | 8/1964 | Alford | 33/812 |
| 4,265,021 | 5/1981 | Campbell | 33/784 |
| 4,972,603 | 11/1990 | Meyer | 33/784 |
| 5,176,516 | 1/1993 | Koizumi | 33/513 |
| 5,685,084 | 11/1997 | Demers | 33/513 |

FOREIGN PATENT DOCUMENTS

| | | | |
|---|---|---|---|
| 541947 | 1/1932 | Germany | 33/513 |
| 56-54303 | 5/1981 | Japan | 33/784 |

*Primary Examiner*—G. Bradley Bennett
*Attorney, Agent, or Firm*—Michael J. Femal

[57] ABSTRACT

A osteological instrument having an unique dual rod and bearing linear motion mechanisms incorporating multiple measuring features and functions providing stable, rigid and generally fluidity of movement of horizontal and vertical caliper arms thereon.

7 Claims, 4 Drawing Sheets

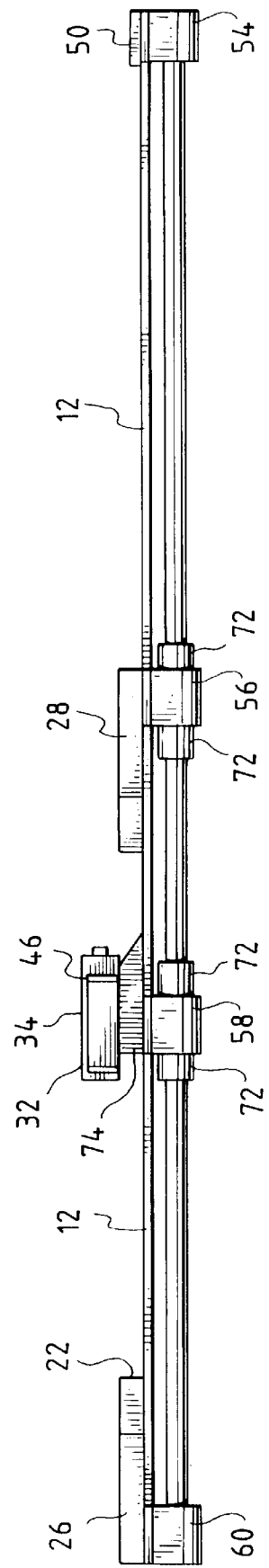

OSTEOLOGIC MEASURING DEVICE

DESCRIPTION

1. Technical Field

The invention relates generally to a osteologic measuring instrument, and more particularly to a an instrument that combines a coordinate caliper, simometer and a traditional caliper into a single osteologic measuring device to facilitate the measurement of humans bones in the study of the structure and function of bones.

2. Background Art

The present day anthropology laboratories include staffs of somatologists that deal with the physical nature and characteristics of man. These science professionals are dependent upon the quality of the instruments used in measuring the various human bones. The design of many osteologic instruments have remained the same even though there has been many advances in materials and types of designs used to communicate information in the present day. The osteologic instruments are often marginal and antiquated instruments in dealing with modern day requirements of more accurate and universal instruments to make various measurements.

For example, the sliding caliper is used for certain cranial measurements in the facial region. The design of this osteologic measurement device has generally remained constant over the years without major improvements in design or accuracy. In addition, various measurements of the head are made with a Western Reserve Model Head Spanner that also has various limitations in its use and accuracy. For many years lab technicians and osteologists concerned with the measurement of the human bones have used these above-mentioned instruments alone or in conjunction with one another such as the caliper and head spanner but with varying success. The measurements taken are dependent upon the skill of the professional taking the measurement but all to often measurements of the same bones taken under the identical conditions by different people of equal skill are inconsistent with one another.

Moreover, none of these above-mentioned osteological instruments either alone or in conjunction with one another have provided easy, quick and accurate measurement of the human skull and other bones in the human body.

SUMMARY OF THE INVENTION

Accordingly, an important object of the present invention is to provide an osteologic measuring device that combines a coordinate caliper, simometer and a traditional caliper into a single osteological instrument.

A further object of the invention is to provide a sturdy, portable, easily manipulated osteologic measuring device that incorporates a slidable vertical caliper with a digital readout for repeatable accuracy in addition to the coordinate caliper.

Another object of the invention is to provide an osteologic measuring device that combines multiple tool functions of a coordinate caliper, simometer and a traditional caliper into an uniquely designed and constructed single osteological instrument to improve reliability in the measurement of human bones that avoids inconsistent measurement readings when done by another professional.

In the preferred embodiment of the invention, the invention is comprised of a fixed caliper member connected to one end of an elongated horizontal scale bar and a horizontal indexing adjustable caliper movable normal to the scale bar to measure the cranial size of a human skull and further including a vertical coordinate index member slidably engaging a digital readout member movable normal the scale bar intermediate the fixed and adjustable calipers and said vertical coordinate member being adjustable and movable to define a second elongated scale bar that is movable perpendicular to the first elongated scale bar whereby the digital readout member slidable along the horizontal scale bar measures a vertical measurement by slidably receiving the second slidable scale bar to providing a digital readout of the distance that the second scale bar moved with respect to the first scale bar.

Other features and advantages of the invention, which are believed to be novel and nonobvious, will be apparent from the following specification taken in conjunction with the accompanying drawings in which there is shown a preferred embodiment of the invention. Reference is made to the claims for interpreting the full scope of the invention, which is not necessarily represented by any one embodiment.

BRIEF DESCRIPTION OF THE DRAWINGS

FIG. 4 is a bottom view of the osteologic measuring device shown in upright position.

DETAILED DESCRIPTION

Although this invention is susceptible to embodiments of many different forms, a preferred embodiment will be described and illustrated in detail herein. The present disclosure exemplifies the principles of the invention and is not to be considered a limit to the broader aspects of the invention to the particular embodiment as described.

Figure 1:
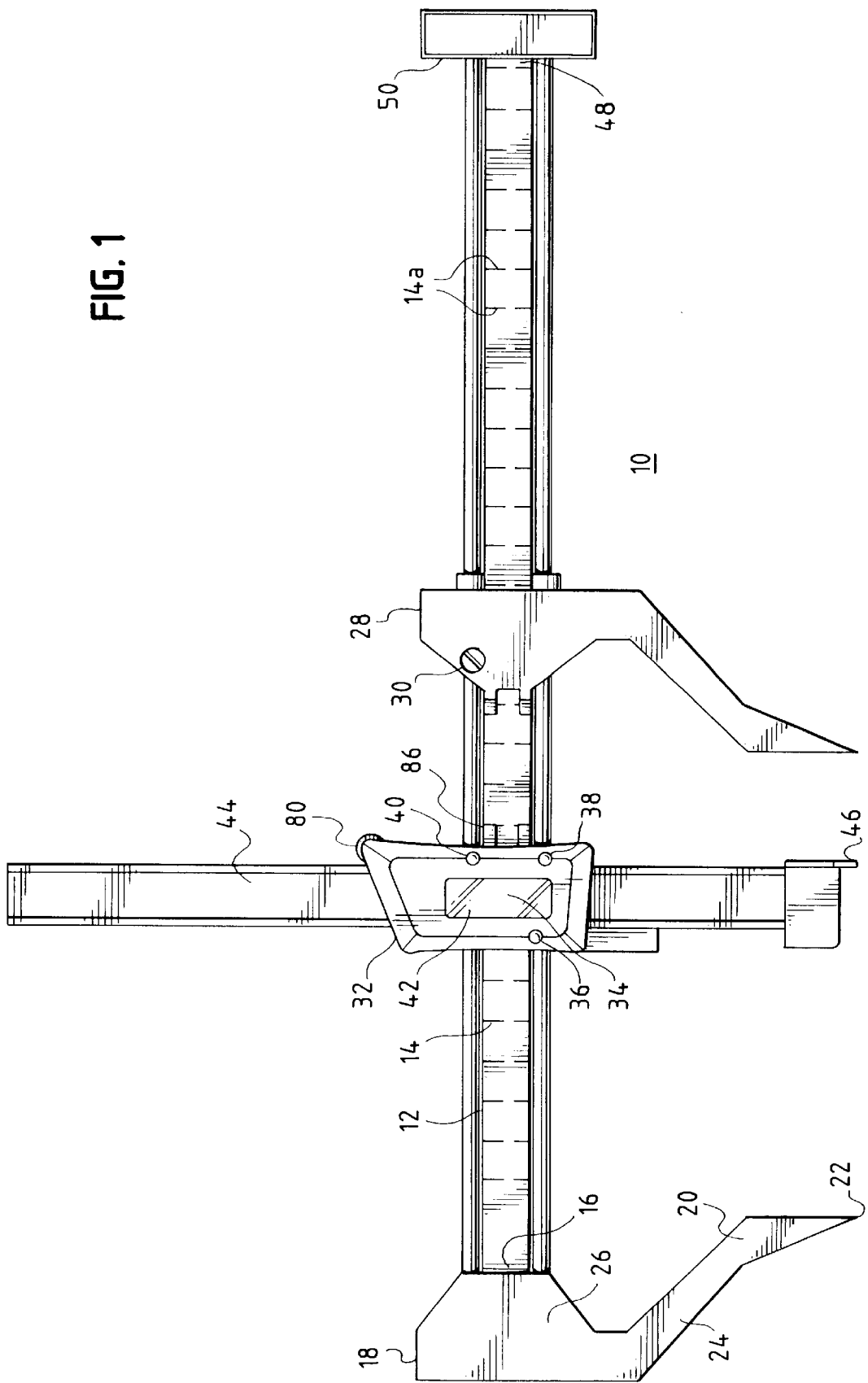
FIG. 1 is a frontal view of the osteologic measuring device according to the present invention.

FIG. 1 shows a frontal view of one embodiment of an osteologic instrument 10, which includes a generally flat, rectangular and elongated scale bar or ruler 12 of a predetermined length having a distance scale 14 in millimeters. The distance scale 14 is marked off longitudinally or horizontally along the length of the ruler 12 in increments of ten millimeters (10 mm) 14a and further includes an upper scale in increments of 0.5 mm and lower scale of 1 mm, both of these scales not shown in FIG. 1. The ruler 12 in the present invention is made out of a flexible steel with a distance scale 14 on its front surface and a blank rear surface. The ruler 12 might also be made out of a plastic, nylon or any other suitable material for making a ruler with a scale bar.

At one end 16 of ruler 12 is a fixed caliper arm 18 located a predetermined distance from the scale increments and irregularly shaped in the form of a goose having a head 20 terminating in a sharp point 22. The top of the head 20 forms a plane that is perpendicular to the horizontal ruler 12. A neck 24 extends downwardly from the head 20 to a body 26 of the goose shaped caliper arm 18. The body 26 is fixedly attached in relationship to the end 16 of the ruler 12. An opposing and nearly identically shaped movable caliper indexing arm 28 in comparison to the fixed arm 18 is slidably mounted onto the ruler 12 to facilitate the indexing of a coordinate that allows recording of subtense along the horizontal plane of the ruler 12. This indexing arm 28 moving horizontally along the ruler 12 allows the measuring of the width of a skull for example by reading a pair of measurements indices 86 having slightly tapered and spaced apart protrusions nearly engaging the scale on ruler 12 to make a measurement. A setscrew 30 on the movable indexing arm 28 is arranged for engagement with a stop to be described later for selected positions of adjustment along the ruler 12 toward and away from the fixed arm 18. The fixed arm 18 and the movable indexing arm 28 are preferably made out of a single piece of stainless steel construction but other suitable materials could be used also.

A vertical linear motion system 32 includes a digital readout meter 34 located intermediate the fixed and movable arms 18 and 28, respectively. The digital meter 34 is movable horizontally along the ruler 12 while intermediate arms 18 and 28. The digital meter 34 comprises an on and zero button 36, an off button 38, a millimeter/inch button 40 and a LED digital readout 42 in either millimeters or inches depending on the setting of button 40. A generally elongated scale bar 44 becomes the vertical coordinate index having a scale in millimeters and inches thereon. The indexing bar 44 passes axially through the digital meter 34 which measures the linear vertical movement of the scale bar 44 through the meter 34 to a target. The bar 44 includes a target tip 46. The target tip 46 is either integral with or attached to the scale bar 44. The scale bar is made of a plastic material and if the target tip is attached thereto then the target tip 46 is made from brass or the like. The vertical linear motion system 32 is known as a DIGIMAX PN 30-440-2, which is a Swiss precision instrument. The scale bar 44 slides longitudinally and axially through the meter 34 to the target, which is touched by the target tip 46. The heads 20 and tips 22 of the arms 18 and 28 form a jaw geometry incorporating a "common zero" point on the horizontal and vertical axis between the tips 22 and target tip 46 allowing the measurement of smaller features relative to prior art designed instruments.

At the other end 48 of the ruler 12 is an end plate 50 that stops the travel of the movable arm 28 along the ruler 12. When the digital readout meter 34 is moved along ruler 12 to its left most position against the body 26 of arm 18, the target tip 46 is positioned immediately above tip 22 of arm 18. Next the movable arm 28 is slid along the ruler 12 to its most left travel and forms a common zero point defined by points 22 and target point 46 all aligned together at a single point. The meter 34 is turned on at this point by button 36 and then the button 36 is pushed again to zero the vertical scale bar 44 at this common zero point with the arms 18 and 28 forming a closed jaw geometry.

Figure 2:
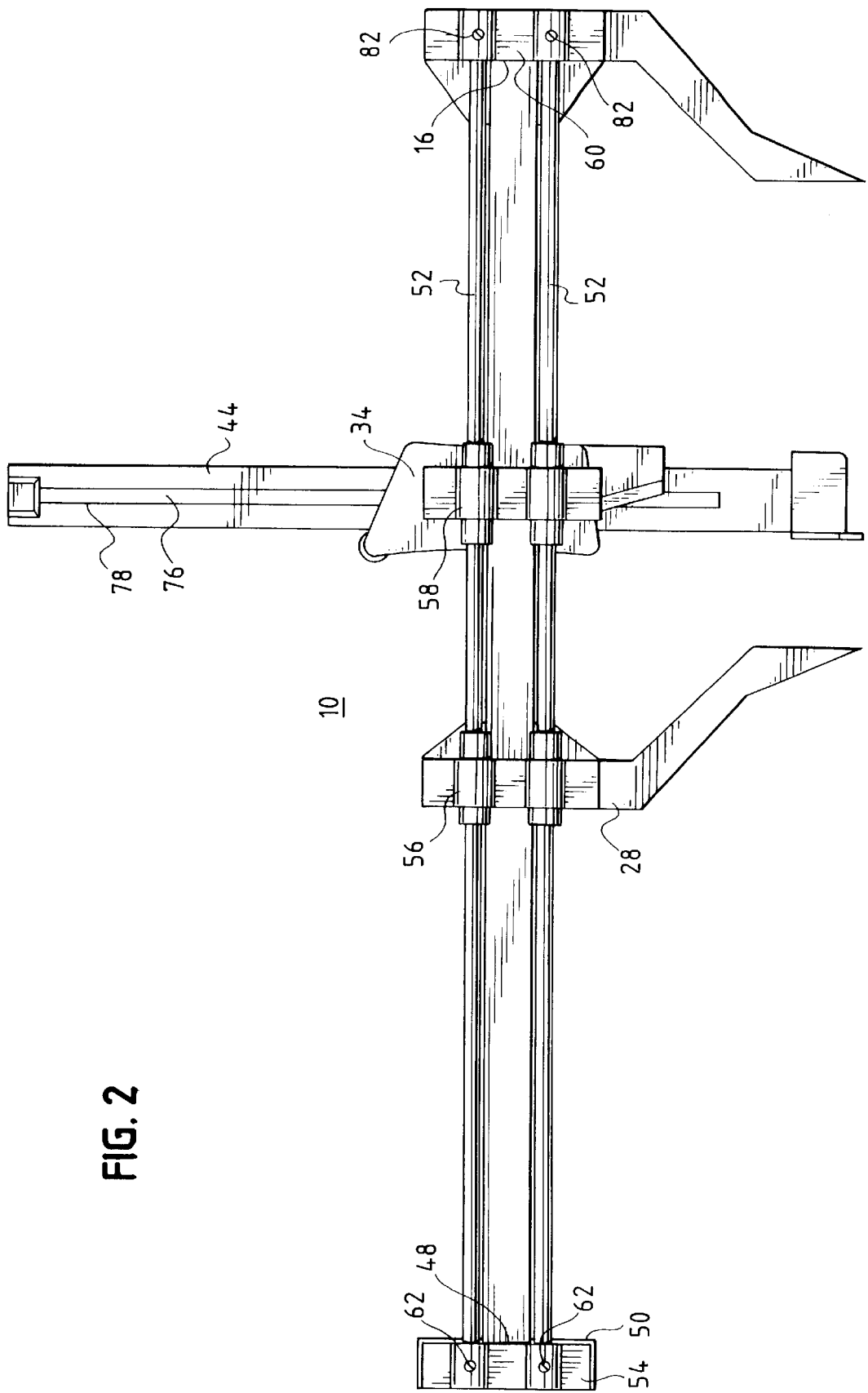
FIG. 2 is a back view of the osteologic measuring device of FIG. 1.

Referring now to FIG. 2, a back view of the osteological instrument 10 is shown. A pair of identical 304 stainless steel precision guidance rods 52 form a dual rod and bearing linear motion system that provides rigidity, fluidity of movement for the meter 34 and movable arm 28 along the ruler 12. The dual rod construction provides these above mentioned advantages plus a decrease in overall weight when compared to prior art linear calipers utilizing a solid longitudinal member. The dual rod linear motion system includes four generally identical aluminum pillow blocks 54, 56, 58 and 60. Pillow block 54 is attached to end plate 50 and captures the other end 48 of ruler 12 in a fixed relationship while receiving each end of guidance rods 52 in a pair of cylindrical holes 64 in a tight or friction fit. In addition, a pair of setscrew 62 may also be used to fixedly attach the rods 52 in cylindrical holes 64. Pillow block 56 includes a pair of cylindrical holes 66 receiving the dual rods 52 axially in a slidable relationship. The pillow block 56 is attached to the movable arm 28. Each cylindrical hole 66 includes a pair of cast bronze guidance bearings 72. Of course, a single cast bronze guidance bearing in each cylindrical hole 66 would work too. The bearings 72 maintain the rigidity and the fluidity of movement of the pillow block 56 and arm 28 horizontally along the guidance rods 52 and ruler 12 during a measurement. Pillow block 58 is attached to a spacer plate 74, which in turn is attached to digital meter 34. The spacer plate 74 also includes a pair of measurement indices 86 tapered in the same manner as the indices 86 on arm 28. This arrangement allows the meter 34 to move horizontally along the dual guidance rods 52 received within a pair of cylindrical holes 68 having the same guidance bearing 72 as pillow block 56 and the ruler 12 in a rigid and fluid motion with a single hand motion by the professional osteologists. An elongated axial guidance bar 76 received within a recess 78 in the backside of the bar 44 slidably engages the scale bar 44 as it extends vertically along the same axis as the guidance bar 76 to maintain rigidity of structure. A thumbwheel 80 on the edge of the meter 34 engages the scale bar 44 to move the scale bar in small increments both vertically and axially through the meter 34 to the target of the vertical-indexing caliper. Pillow block 60 is attached to the ruler 12 at the one end 16 and the dual rods 52 are tightly fitted into a pair of cylindrical holes and a pair set screws 82 may be used to anchor the other end of the dual rods 52.

Figure 3:
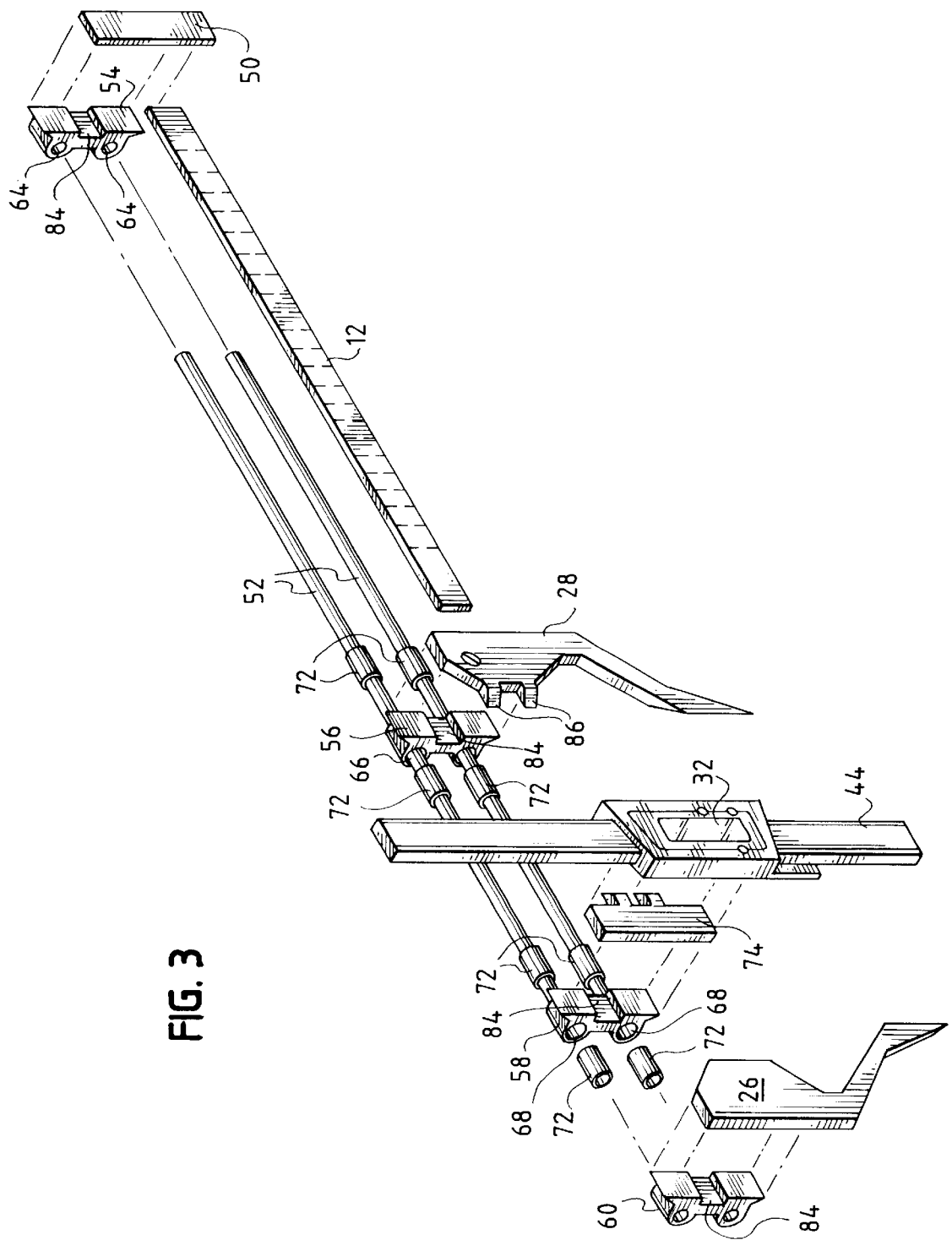
FIG. 3 is an exploded view of the osteologic measuring device of FIG. 1 showing several parts of the osteologic instrument of the foregoing Figs.

Turning now to FIG. 3, an exploded view of the parts comprising the osteological instrument made in accordance with the invention is shown. The previous specification describes most of the parts in this view. However, each pillow block 54, 56, 58 and 60 includes a generally rectangular recess 84 having approximately the same width as the ruler 12 and a depth of approximately the same or greater than the thickness of the ruler 12 so that the ruler 12 is received within the recess 84 of each pillow block when the instrument is fully assembled. This rectangular recess 84 in each pillow block in conjunction with the ruler 12 forms a rigid steel beam structure for further rigidity of structure and a rigid and stable base for holding the dual guidance rods. This overall construction provides the strong yet lightweight construction of the present invention that prior art devices lacked.

In FIG. 4, a bottom view of the osteological instrument 10 is shown. Ruler 12 is spaced a predetermined distance above the dual guidance rods 52 by the pillow blocks 54, 56, 58 and 60. The set screw 30 is turned downwardly when the proper position is reached on the ruler 12 through the pillow block into a frictional engagement on one of the dual rods 50. The thumbwheel 80 on the meter 34 is turned and engages the side of the scale bar 44 to move the scale bar 44 vertically forward to engage the target.

In operation, the movement of the arm 28 and the vertical measuring meter 34 on the horizontal measuring surface is best accomplished by grasping the body 26 of traveling arm 28 or the meter 34 intermediate the dual parallel rods 52 and sliding these elements gently. If attempting to adjust the measurement more precisely, the osteological instrument may be grasped by the dual guidance rods 52, but care must be taken not to squeeze the rods 52 together as this action will lock the arm 28 and meter 34 in place. Once positioned, the horizontal jaw of arm 28 may be locked down via the thumb or set screw 30 onto one of the rods 52. Only moderate tightening of the thumbscrew 30 is required to accomplish this. The thumbscrew 30 should not be over tightened onto the dual rods 52, as this may damage the cast bronze bushings if done repeatedly. To zero the coordinate index, spread the jaws to about 150 mm, holding the instrument perpendicular to a flat surface and place the tips on that surface. Gently pushing the coordinate index to the surface and pressing the "ON" button 36. To compare the vertical distance between two points, zero point may be reset at any level. The approximate full range measurement on both horizontal and vertical axis is 250 mm+ on the horizontal analog scale and +70 mm to −50 mm on the vertical digital scale. In addition, the digital meter 34 might include a digital interface for connection to a miniprocessor or personal computer through a standard RS-232 port for automated data collection and processing of Subtense measurements. Still further the movable arm 28 might include a digital meter mounted in a horizontal orientation and attached to the top of the body 26 of arm 28 with a guiding scale passing axially through the meter to form a scale bar reference for the meter. These and other improvements would be within the realm of an ordinary person skilled in the art of osteological instruments once reviewing this invention.

Having described and illustrated the principles of the invention in a preferred embodiment thereof, it should be apparent that the invention can be modified in arrangement and detail without departing from the spirit and scope of the invention as claimed.

I claim:

1. A osteological instrument comprising:

an elongated generally flat, rectangular scale bar of a predetermined length and thickness having a front surface with a scale, a back surface, a top, a bottom and two ends, a pair of guiding rods of a predetermined length of approximately the same length as said scale bar, a first pair of blocks spaced a predetermined distance apart from one another having at least two holes therein for receiving said rods in a stationary and fixed position attached to the opposing ends of each rod and a second pair of blocks having at least two holes therethrough for receiving said rods in a movable and slidable relationship therewith, said first and second pair of blocks holding said rods in a generally parallel relationship with respect to one another and spacing the guiding rods below the back surface of the scale bar a predetermined distance, recess means on each block for receiving said scale bar in a fixed relationship with the first pair of blocks and in a guiding and slidable relationship with the second pair of blocks, a pair of generally irregularly shaped arms extending downwardly and slightly angled apart from one another in which one arm is connected to one of said fixed blocks at one end of the scale bar and the other arm is connected to one of said movable and slidable blocks with respect to said scale bar to form a jaw geometry for measuring human bones, a digital meter connected to the other movable block located intermediate the one arm connected to the fixed block and the other arm connected to said movable and slidable block and guided and slidable along the pair of rods passing axially through said movable block with respect to the scale bar having an axial passage therethrough for slidably engaging a second vertical scale bar movable through said meter axial passage to a vertical target whereby the arms and vertical scale bar can be zeroed together as a common reference point when the jaws of the arms are together and the vertical scale bar is adjacent to the jaws of said arms.

2. The osteological instrument of claim 1, wherein each arm is in the shape of opposing geese having their heads terminating in a sharp point coming together to form a closed jaw geometry generally perpendicular to and along a horizontal plane with respect to the scale bar to measure the width of a human skull or the like.

3. The osteological instrument of claim 2, wherein the fixed and movable arms are made from stainless steel.

4. The osteological instrument of claim 1, wherein the first and second pair of blocks are generally rectangular pillow blocks of identical dimensions having a generally flat to surface and a knurled bottom surface, opposing sides and ends wherein the pair of holes in each block are parallel to each other and extend through the blocks from one side to the other, each block having a generally rectangular recess in the top surface intermediate it opposing ends to receive said rectangular scale bar.

5. An osteological instrument comprising:

a) An elongated generally flat, rectangular scale bar or ruler 12 of a predetermined length and thickness having a front surface with a distance scale 14 for making measurements of a human bone, an opposing blank rear surface, a top, a bottom and two ends;

b) a pair of guiding rods 52 of a predetermined diameter and length approximating the length of said bar scale;

c) four rectangular pillow blocks 54, 56, 58 and 60 having a generally flat rectangular top surface, a knurled bottom surface, a pair of opposing sides and ends, a pair of spaced apart holes 64,66, spaced a distance slightly greater than the width of the ruler 12 and axially parallel to one another having a slightly greater diameter than the rods extending through one side of the pillow block to the other side near the knurled bottom surface, each block includes a generally rectangular recess 84 on the top surface intermediate the ends of each block and extending from one side to the other side thereof having approximately the same width as the ruler 12 and a depth of approximately the same or greater thickness than the ruler 12, said pair of dual guiding rods 52 having one pair of ends fixedly connected within the holes 64 of one pillow block 54 and having the other pair of ends fixedly connected to the pair of holes 64 of the second pillow block 60 so that the guiding rods 52 are mounted within said one and second pillow blocks 54 and 60, respectively, in a spaced apart and parallel relationship with respect to one another;

d) a rectangular plate end cap 50 approximating the dimensions of the top surface of the one pillow block 54 for attaching to the top surface of the pillow block when one end of the scale bar 12 is within the recess 84 of the block to secure the scale bar in a fixed and stationary position;

e) guidance bearings 72 mounted within each hole in the third and fourth pillow blocks 56 and 58 for slidably receiving said parallel rods therethrough so that the pair of blocks are slidably guided along the length of the scale bar by the pair of rods 52 passing through the holes 66;

f) a pair of opposing generally goose shaped caliper arms 18 and 28 each having a head 20 terminating in a sharp point 22 with the top of each head forming a plane that is perpendicular to the scale bar 12, each arm extending generally perpendicular away from said bar scale 12 and parallel rods 52 to form a jaw geometry for measuring human bones, one measuring arm 18 fixedly and stationary mounted to the top surface of the pillow block 60 to lock the other end of the scale bar 12 in place, the second movable caliper indexing arm 28 is mounted to the top surface of the third pillow block 56 includes a pair of measurement indices 82 having two slightly tapered and spaced apart protrusions nearly engaging the scale of the ruler 12 for making measurements such that the scale bar 12 is received within the rectangular slot formed by the second arm 28 and the recess within the top surface of the third pillow block 56 to guide the indexing arm 28 along the top surface of the scale bar for measuring the width of a human skull with relationship to the fixed one arm 28;

g) a digital readout meter 34 provides a vertical linear motion system located intermediate the fixed and movable arms 18 and 28, respectfully, the digital meter having an on and zero button 36, an off button 38, a millimeter/inch button 40 and a LED readout 42 adjustable to either millimeters or inches, said meter 34 having a spacer plate 74 attached one side to the top surface of pillow block 58 and the other side attached to the meter 34, said spacer plate including a pair of measurement indices identical to the indices 86 on the movable indexing arm 28; and h) a generally elongated scale bar 44 forms a vertical coordinate index having a suitable scale in millimeters or inches, said scale bar 44 passes axially through the digital meter 34 to a target to be measured and includes a target tip 46 wherein, the heads 20 and tips 22 of the arms 18 and 28 form a jaw geometry incorporating a common zero point on the horizontal and vertical axis between the tips 22 and target tip 46 allowing the measurement of smaller human skull and bone features like nasal passages or the like.

6. The osteological instrument of claim 5, wherein the digital meter 34 is a Swiss precision instrument named a DIGIMAX PN 30-440-2.

7. The osteological instrument of claim 5, wherein the bearings 72 are a pair of cast bronze guidance bearings maintaining the rigidity and the fluidity of movement of the pillow blocks 56 and 58 and indexing arm 28 and meter 34 horizontally along the guidance rods 52 and ruler 12 during a measurement.

* * * * *